United States Patent
Lange et al.

(10) Patent No.: US 6,942,697 B2
(45) Date of Patent: Sep. 13, 2005

(54) PAIR OF LUMBAR INTERBODY IMPLANTS AND METHOD OF FUSING TOGETHER ADJOINING VERTEBRAE BODIES

(75) Inventors: Robert Lange, Paris (FR); Jacques Commarmond, Châteauroux (FR); Armand Linge, Richterswil (CH)

(73) Assignee: Co-Ligne AG, Zurich (CH)

( * ) Notice: Subject to any disclaimer, the term of this patent is extended or adjusted under 35 U.S.C. 154(b) by 0 days.

(21) Appl. No.: 10/739,529

(22) Filed: Dec. 19, 2003

(65) Prior Publication Data

US 2004/0186572 A1 Sep. 23, 2004

(30) Foreign Application Priority Data

Dec. 19, 2002 (EP) .............................. 02406120

(51) Int. Cl.[7] .................................................. A61F 2/44
(52) U.S. Cl. .................................................. 623/17.11
(58) Field of Search ............................ 606/61, 63, 76, 606/78; 623/17.11, 17.12, 17.13, 17.15, 17.16, 23.47, 23.5

(56) References Cited

U.S. PATENT DOCUMENTS

| | | | | |
|---|---|---|---|---|
| 5,607,424 A | * | 3/1997 | Tropiano | ...................... 606/61 |
| 5,766,252 A | * | 6/1998 | Henry et al. | .............. 623/17.16 |
| 5,888,224 A | * | 3/1999 | Beckers et al. | ........... 623/17.16 |
| 6,224,631 B1 | * | 5/2001 | Kohrs | ...................... 623/17.11 |
| 6,241,770 B1 | | 6/2001 | Michelson | |
| 6,245,108 B1 | * | 6/2001 | Biscup | ...................... 623/17.11 |
| 6,468,311 B2 | * | 10/2002 | Boyd et al. | .............. 623/17.16 |
| 2002/0138146 A1 | | 9/2002 | Jackson | |
| 2002/0161443 A1 | * | 10/2002 | Michelson | ............... 623/17.11 |

FOREIGN PATENT DOCUMENTS

| | | |
|---|---|---|
| EP | 0732093 | 9/1996 |
| WO | WO-00/44318 | 8/2000 |

* cited by examiner

*Primary Examiner*—Kevin Shaver
*Assistant Examiner*—David Comstock
(74) *Attorney, Agent, or Firm*—Browdy and Neimark, PLLC

(57) ABSTRACT

The pair of lumbar interbody implants is designed to be pushed laterally in a space between adjacent vertebrae for replacing the disc between these vertebrae. Each implant comprises a first and a second saggital wall and an anterior wall at one end and a posterior wall at the other end. The two implants are asymmetric to each other and are therefore more appropriate for the transforaminal lumbar interbody fusion. Preferably a first implant has a first saggital wall with an outer surface that is curved and a second saggital wall that is essentially plane.

19 Claims, 5 Drawing Sheets

Figure 3:
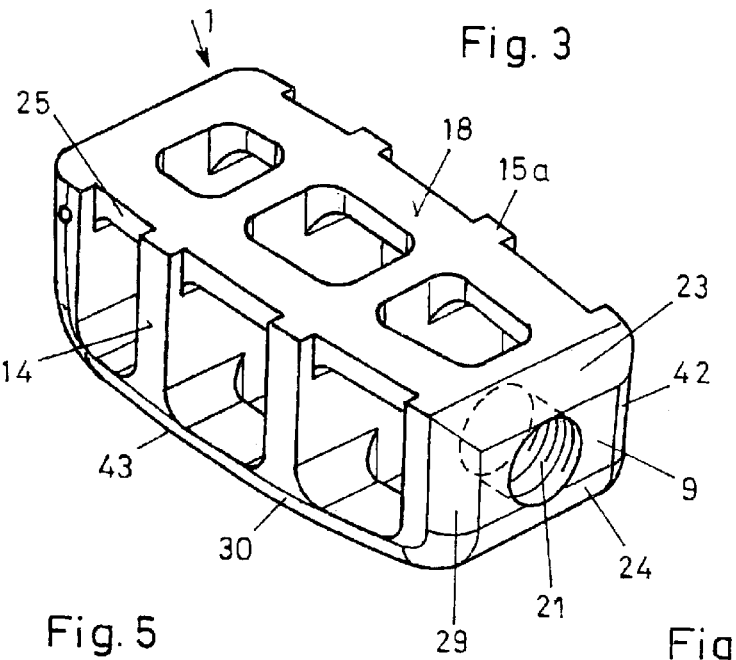

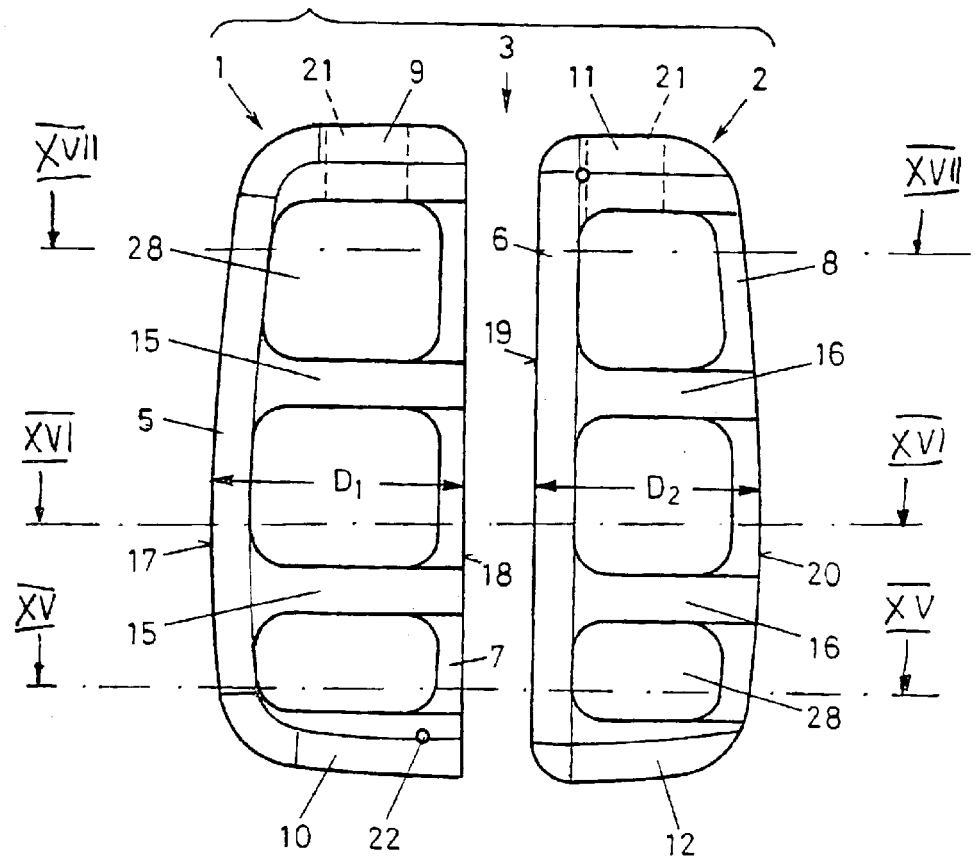
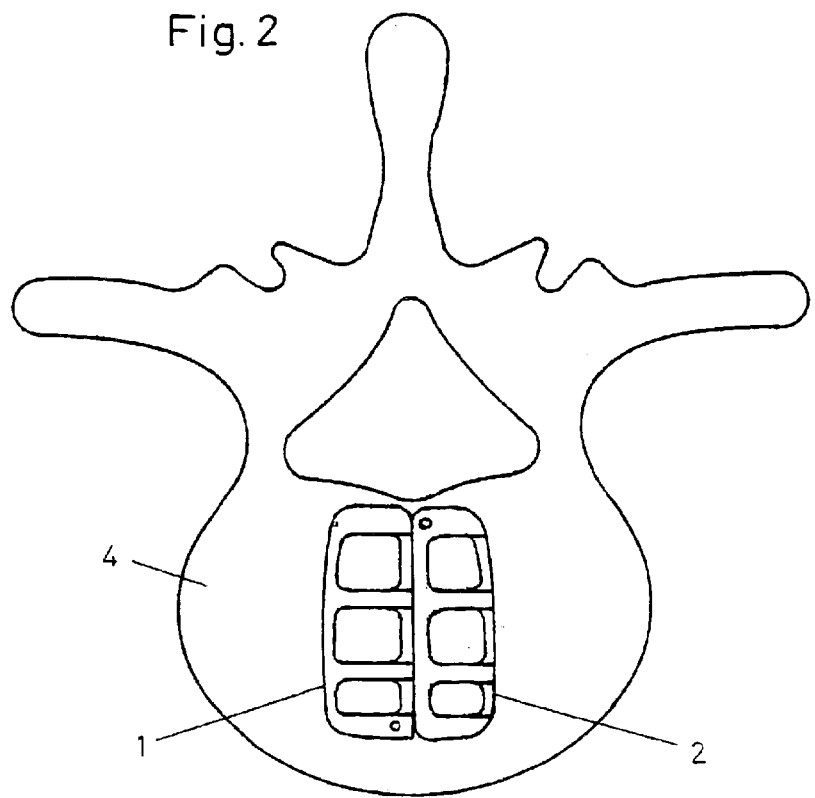

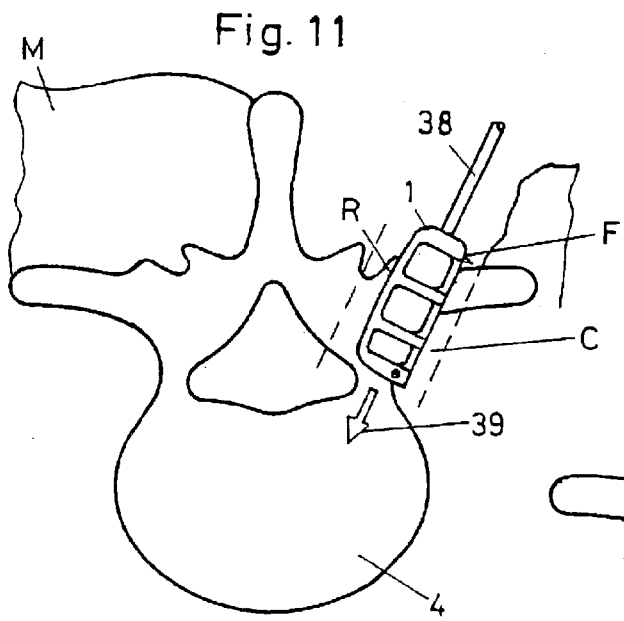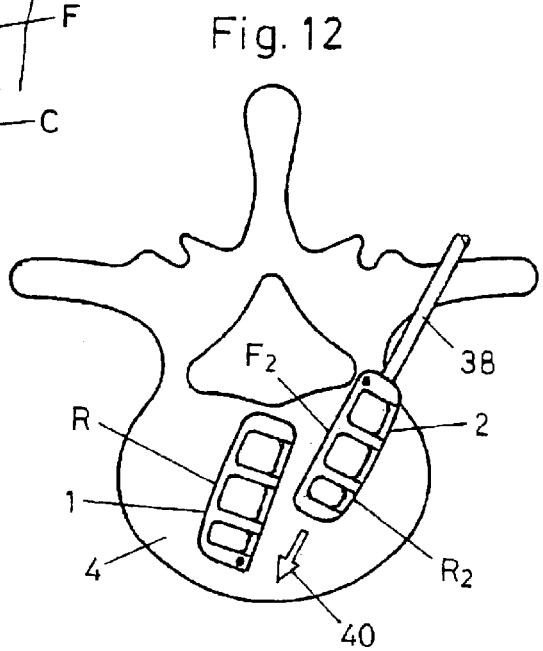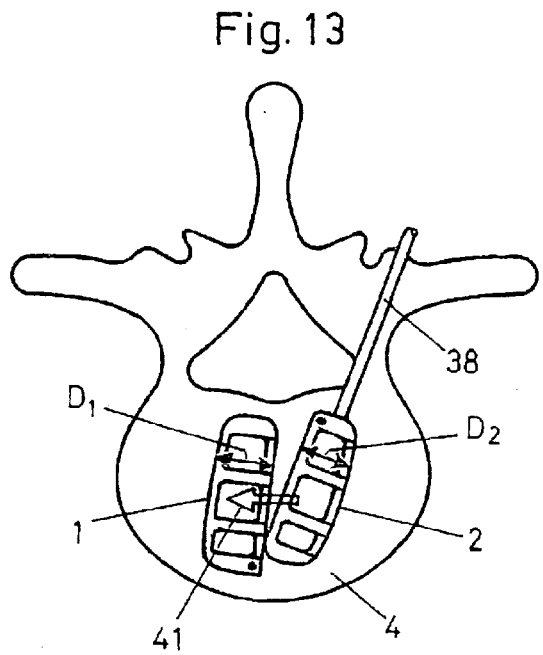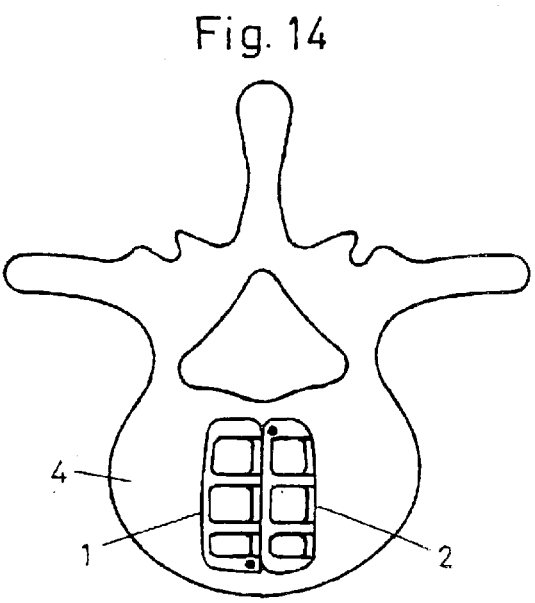

PAIR OF LUMBAR INTERBODY IMPLANTS AND METHOD OF FUSING TOGETHER ADJOINING VERTEBRAE BODIES

The invention relates to a pair of lumbar interbody implants designed to be pushed laterally in the disc space between adjacent vertebrae for a spinal, interbody fusion.

WO 00/44318 (Commarmond) discloses an interbody implant being in the form of a cage. It has a top edge and a bottom edge to provide at least a retaining ridge. The cage enables posterior approach insertion in the space between adjacent vertebrae and a lateral shift to a locking position in the intervertebral space. The retaining ridge prevents the cage from slipping in a sideways or lateral direction.

U.S. Pat. No. 5,607,424 (Tropiano) discloses a lumbar interbody cage having upper and lower surfaces that provide a more anatomical contact with the abutting surfaces of the vertebral interspace.

Debilitating back and leg pain is one of industrialized society's most pervasive source of infirmity. In spite of more and more sophisticated technology, the exact causes of leg and back pain are not exactly known for each individual. However, pain symptoms are often associated with the degeneration of specific structures in the spine, which can become painfully unstable, thought to cause back pain, or compress a neural structure, which are believed to be a source of leg pain. In most cases, a spinal fusion is designed to decompress painful nerve root impingement and to eliminate painful movement by fusing two or more vertebrae together in a controlled and aligned fashion.

To those familiar with the art, the spine being is thought to be composed of many motion segments, each one consisting of a weight bearing disc, two adjacent vertebral bodies and their respective pedicles, as well as the posterior facet joints, the lamina and spinous and transverse processes. The disc's primary role is to bear weight, and allow a few degrees of bending and rotation at each motion segment. The bilateral posterior facet joints have a stabilizing role, preventing dangerous translation of two vertebral bodies and too much rotation of the motion segment, which could damage neural structures.

The dural sac runs adjacent to the posterior aspect of the vertebral body. It contains nerves, which extend to various parts of the body. The surrounding structures of the vertebral column form the spinal canal and protect the dura from trauma and allow motion. At each motion segment, the spinal canal is composed of the posterior wall of the disc, the pedicles, the vertebral body and the posterior elements. It should be noted, that the spinal canal is quite vascular and when retracted for a surgical procedure, can cause excessive bleeding. At each motion segment, the exiting nerve roots pass out bilaterally, from the dura within the spinal canal, through corresponding neural foramen, which are formed bilaterally by the pedicle, the facet joints and posterior disc.

Degeneration of a spinal segment is marked by a cascade of events, where the disc develops small tears, possibly resulting in a painful and nerve compressing herniations. This can be caused by any combination of age, trauma or disease. The disc gradually will collapse like a deflated tire and then bulge into the vertebral canal while foramen close upon the nerve roots, causing compression, which in some patients is a great source of pain felt in the legs.

As the degenerative process advances, the facets joints and disc can create hypertrophic bone growths, creating bone spurs, which can further compress the neural structures, and cause additional pain, neurological abnormalities such as partial loss of sensation or ability to move.

This cascade of events can occur in one or many motion segments of the spine, each with varying degrees of degeneration and presumed source of pain. All spines show some degrees of this process, as a person ages. Some patients find the various phases in these events to be intolerably painful and incapacitating, due to what can be termed neural compression and segmental instability. Yet other patients, in spite of such spinal degeneration, continue to function. Where several motion segments show degeneration, some segments can be the source of pain, while others not. The reasons for these seemingly contradictory observations are not entirely understood. This complicates the surgeon's choice of which motion segment to treat to reduce the patient's pain and return him to function.

Certain suffering patients, and certain painfully degenerative spinal motion segments, can be improved with a procedure called a spinal fusion. The spine surgeon is thus challenged to determine which motion segment might be the source of the patient's predominate pain, and which patient might benefit from the operation. The surgeon's goal will be to decompress the painful impinging structures on the nerves and then to stabilize one or several motion segments, often using implants, including cages, which are the subject of this invention. The implants hold the operated motion segment in proper alignment so that two or more vertebral bones may grow together over several months, forming one continuous bone. This blocks painful motion, leaving the formerly impinged nerves decompressed. Because the spine is comprised of many motion segments, like the links in a chain, normal motion of the spine is still possible due the mobility of the segments above and below the fusion. In fact, because all human spines are settling as a patient ages, some without pain, it is thought a spinal fusion is a controlled version of a natural process, in a manner that will avoid pain.

There are several types of implants used to stabilize a motion segment for spinal fusions. Interbody cages are used between the vertebral bodies, to bear weight where the disc was removed, between the vertebral bodies. Such cages are most often filled with an osteoinductive material, in most cases the patients own bone, or more recently a bone substitute, which promote bone cell growth through and around the cage to the adjacent vertebrae to become fused. Where the posterior structures are decompressed and destabilized, cages are often associated with additional anchor and stabilizing mechanisms such as pedicle screws, laminar hooks, plates and rods, which together with the cages, serve as sort of a scaffolding that holds the vertebral segments in a stable alignment while bony fusion occurs and the vertebra grow together. At this point, the implants loose their stabilizing role, which is taken over by viable bone. The assembly of decompressed motion segment, cages and associated implant, along with an osteoinductive material is what practitioners of spinal fusion call a "fusion construct."

Thus each spinal fusion has the goal to eradicate the source of pain, by stabilizing what is painfully mobile, and decompressing what painfully compresses a nerve. The surgeon achieves this by resection of the compressive structures, stabilizing the motion segment in alignment with implants, and the proper management of bone cell biology so that the motion segment will grow together over several months into one continuous bone. During the formation of healthy bone between the vertebrae of a bone segment, there is a race between the mechanical fatigue resistance of the implants and weight bearing bone. The goal is for the bone to take over the weight-bearing role of the construct after several months. If fusion does not occur, over time the implants will break and fail. After a successful fusion, and although implants no longer have a stabilizing or weight bearing role, spinal implants are seldom removed, as it felt that the additional risks of infection or additional trauma from another surgery would out weigh the possible benefit of removing the implant. Therefore most spinal implants remain in the body for the rest of the patient's life.

When a spine surgeon wishes to perform a spinal fusion with implants, he has several surgical approaches and techniques to build a fusion construct, each with its advantages, risks and short-comings. From a general sense, the spine surgeon wishing to perform a spinal fusion is faced with a dilemma. On one hand to generously expose soft tissue and bone to allow proper neural decompression, and implant insertion, with proper segmental alignment and correction. On the other hand, to avoid excessive trauma from the approach. Excessive dissection of a surgical approach, makes the procedure easier for the surgeon, but destroys viable tissue, leading to damage of the surrounding muscle groups, which the body later uses to keep the entire spine in dynamic equilibrium. Furthermore, decompression of the posterior elements, in particular the facet joints, while relieving nerve impingement, can further destabilize the spinal segment to be fused, not allow the fusing bone graft to properly vascularize and reduce the probability of the vertebrae of spinal construct to grow together. Therefore, each of the various techniques available to the surgeon, represent a compromise between the goals of sufficient dissection and decompression, and the need to inflict minimal trauma or instability on the segment to be fused.

Interbody cages are valuable because they place an immobilizing support and fusing bone graft material, where most of the natural load upon the spine can be found, the interspace. Because the cage's role is to bear weight where the disc once was, it is thought that more disc space covered with a cage and bone graft and the better the fit between surfaces of the cage and vertebrae, the more stable the resulting weight bearing fusion construct. A stable but not too rigid construct is desired to allow the bone cells to recognize weight bearing, which is required for the formation of healthy bone. Furthermore, the disc space must be filled as much as possible with bone cells and supporting surface of the cage. When the surgeon desires to place his cages from the posterior approach, usually because he must perform decompression at the same time within the canal, he must go around the dura and avoid trauma to the exiting nerve roots. As a maximum of disc space must be filled with the bone and cage construct the question from the posterior approach becomes, how to provide bi-lateral support avoiding the neural structures. Furthermore, some patients requiring a fusion have had a previous failed spinal surgery, such as a removal of a herniated disc. This leaves scar that is difficult to dissect from the surrounding neural tissues without damage.

Traditionally, spine surgeons use a bilateral, Posterior Lumbar Interbody Fusion (PLIF) technique. Here a portion of the lamina, and the interior of both facets are removed, so the cages may be placed bilaterally into disc space, to the left and right past the dural sac, leaving two bilateral cages within the interspace and a stable support where the disc once was. Because cage passage for this bilateral construct requires the partial dissection of both the facet joints, it destabilizes the motion segment. Therefore pedicle fixation is often used in conjunction with the PLIF procedure. This is quite satisfactory from a neurological and biomechanical, point of view. It allows full decompression of the offending pathology within the motion segment, and provides stable alignment and support with bilateral cages, bone graft in the interspace and pedicle fixation that replace the role of the resected facet joint. However this is accomplished at the cost of sever dissection of the muscle groups of the approach, and at times, a complex and risky passage through scar tissue on previously operated motion segments. These observations have lead surgeons to search for constructs and surgical approaches with the same biomechanical and neurological results, but with less destruction to the surrounding tissue.

The transforaminal approach and technique is disclosed in "Rivista die Neuroradiologia 12 (Suppl. 1): 107–110, 1999" by J. Commarmond and others, and is thought to be an alternative with some attractive qualities. This technique allows placement of bilateral cages, but dissects only one side of the paraspinous muscles, one facet joint as opposed to two for a PLIF procedure. In the case of a PLTF procedure, a surgeon must dissect and disrupt two sides for bi-lateral placement of the cages. This is fine when both sides require dissection for treatment of the neural compression, but there are certain cases where degeneration and the resulting symptoms are thought to come predominantly from one side. Therefore the therapeutic requirements to decompress a facet joint concern one side and not the other.

Typically such patients complain of neurogenic pain predominantly from one side, and it is often with transforaminal approach that the facet joint of the spine can be removed only from the painful side to prepare placement of the cages. The healthier side is avoided and thus muscular, neuro and vascular tissue is preserved. For revision cases, previously operated cases, dangerously adhering scar tissue can be avoided. Thus the transforaminal procedure is unilateral in its approach and builds a bilateral construct described bellow. Decompression and tissue damage is made for reasons of pathology, and less the building of a stable construct.

Transforaminal Technique

Decompression is made from one side. The disc is exposed and its material is removed from one side. The goal at this moment is to eliminate cartilaginous tissue that will prevent formation of bone, and expose subcondral bone with good vascular supply for the bone graft, and to allow space for the first and second cage. A pathway for a pair of dissimilar cages is created laterally from an entry point just bellow the resected facet joint. Again this is usually the side where the most nerve root compression is located, or in the case of a second surgery such as a herniated disc, from the side where no scar tissue has been formed.

To allow insertion of the first and the second cage, disc space height restored using interspace spreaders. The far lateral cage is first pushed into the space. It is designed to go the furthest into the disc space laterally; its leading surface has a distraction and therefore decompression role of the contra lateral foramen. It is pushed part way laterally with an instrument and surfaces are designed for a lateral distraction of the interspace and anchoring once in place. The second cage is inserted through the same incision. Its has a surface that mates with the first cage, which helps push the first to its far lateral position.

The two cages are designed to help to restore the spine to its normal condition, that is restore disc space height, open the foramen to make a nerve decompressing passage, and provide proper lordosis. This unilateral posterior approach is especially suitable when nerve root impingement is purely unilateral, after a failed vertebral operation.

OBECTIVE

An objective of this invention is to provide a pair of lumbar interbody implants which is more appropriate for the transforaminal lumbar interbody fusion technique.

SUMMARY OF THE INVENTION

In accordance with the invention, a pair of lumbar interbody implants is provided designed to be pushed laterally in the disc space between adjacent vertebrae for spinal, interbody fusion.

Each implant comprises a first and a second saggital wall, an anterior wall at one end and a posterior wall at the other end. The posterior wall has means to receive a positioning tool. The implants further comprise an upper surface and a bottom surface. The first and second saggital walls each of which has an outer surface and top and bottom edge. The two implants are asymmetric to each other. The asymmetry of the two implants does not relate to minor differences such as different markers.

Each implant according to the invention is designed to perform a sequence of functions during insertion into the disc space. The requirements of each step of the operation are different, and therefore so are the first and the second implant.

According to a further embodiment of the invention the first implant has a rounded lateral side, which enters first. This helps to ease insertion and the implant to move laterally into disc space and restore the disc space height, opening a nerve root compressing foramina. This also can restore the balance of the spinal segment by providing lordosis of the segment.

According to a further embodiment of the invention the second implant has rounded edges on a far lateral side. The near lateral side is flat with pronounced corners that engage in the bony end-plate when the patient stands or ambulates. This feature prevents undesirable cage migration, which can prevent vasculization of the bone graft and exclude fusion, or displace to create compression on a nerve structure with its associated complications.

According to a further embodiment of the invention, the far lateral side of the second implant is flat and mates with the first implant in order to push the first cage further laterally and to better restore the disc space height, which again opens the far lateral foramen and therefore releases pressure on the nerve roots. It also provides better support under axial load when the patient is ambulating and weight heaving.

According to a further embodiment, at least one of the implants has upward struts designed to make insertion of the implant into the disc space easier and to prevent anterior as well as posterior migration of the inserted implant.

According to a further embodiment of the invention at least one of the implants is shaped with the posterior portion that is not as high as the anterior portion providing lordosis.

According to a further embodiment of the invention the second implant is smaller than the first implant.

Figure 5:
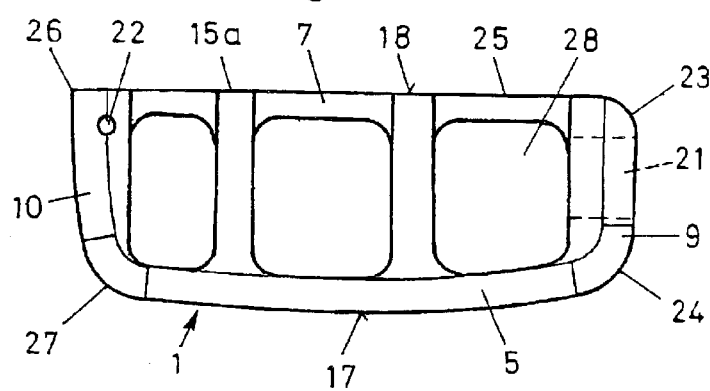
Figure 6:
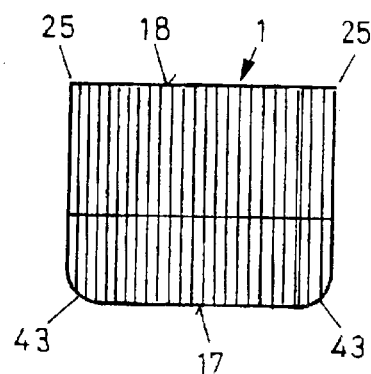
Figure 4:
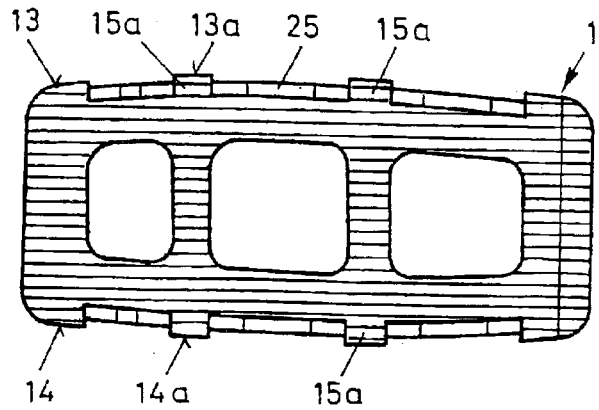
Figure 7:
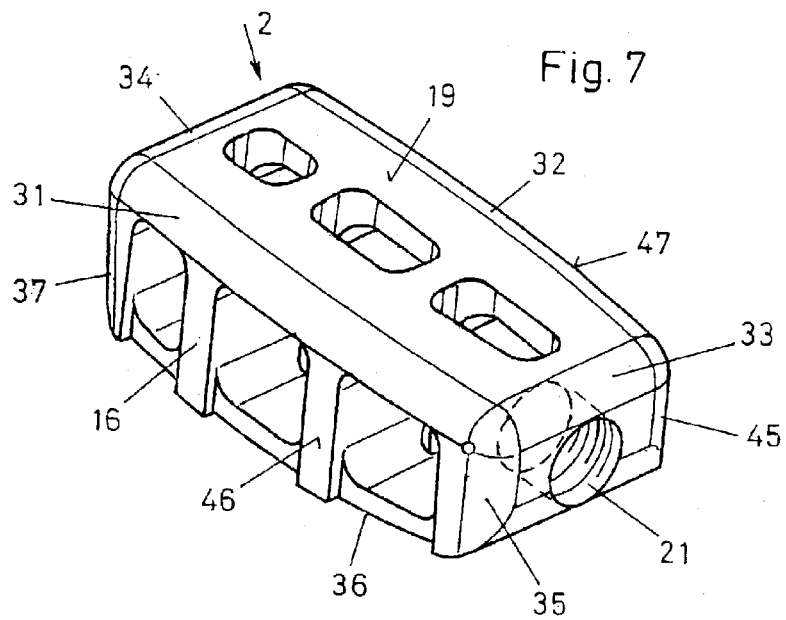
Figure 8:
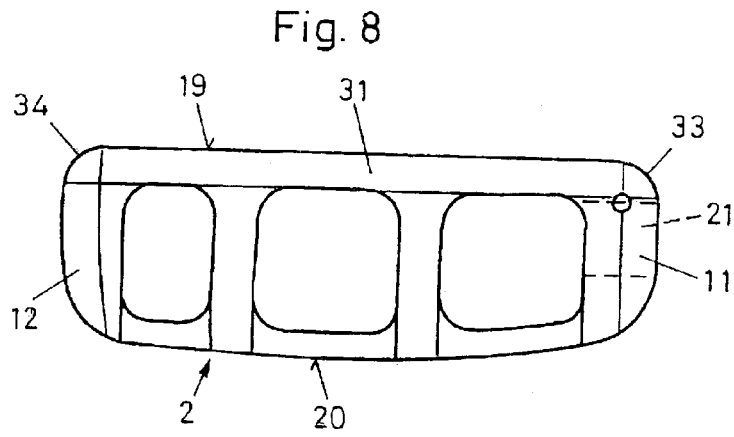
Figure 9:
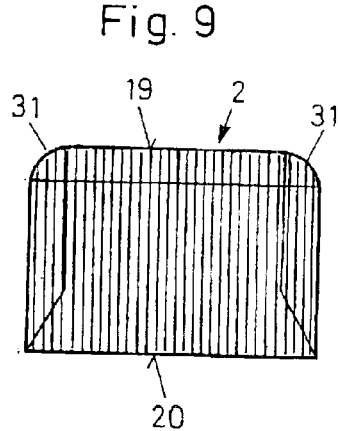
Figure 10:
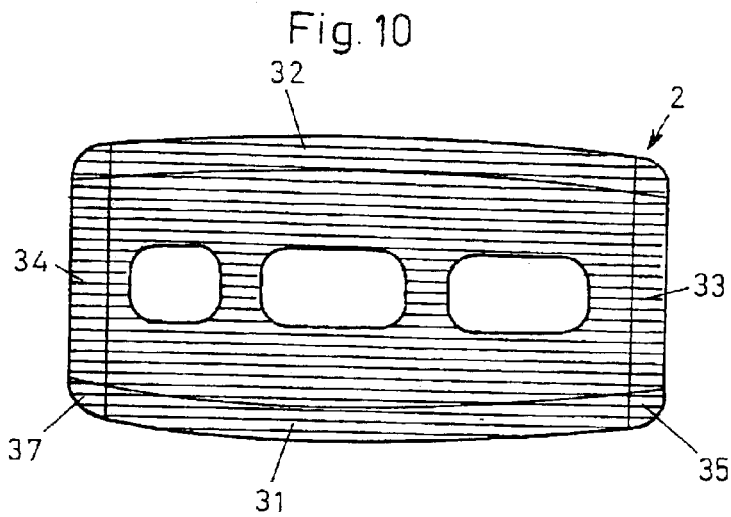
Figure 15:
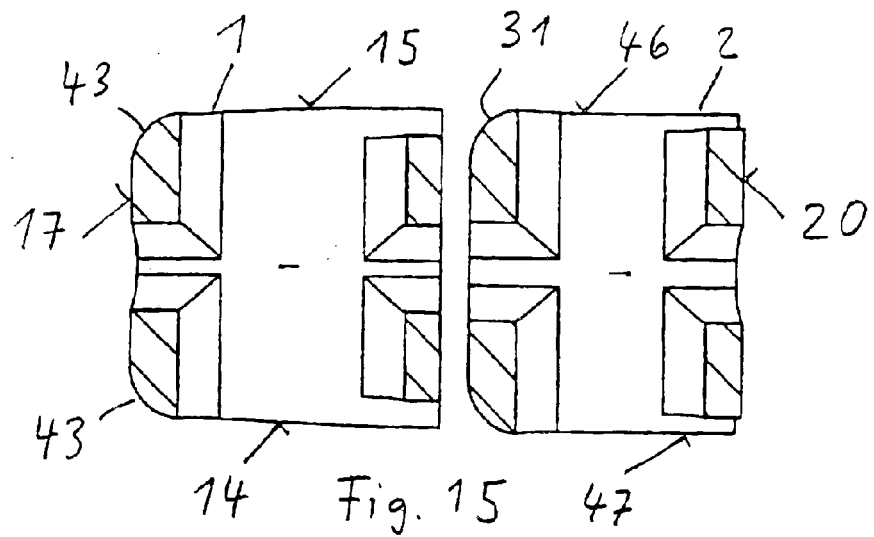
Figure 16:
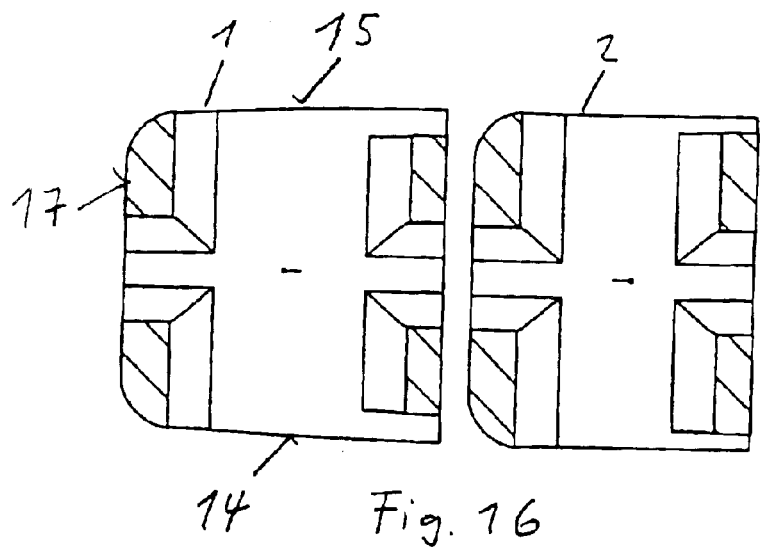
Figure 17:
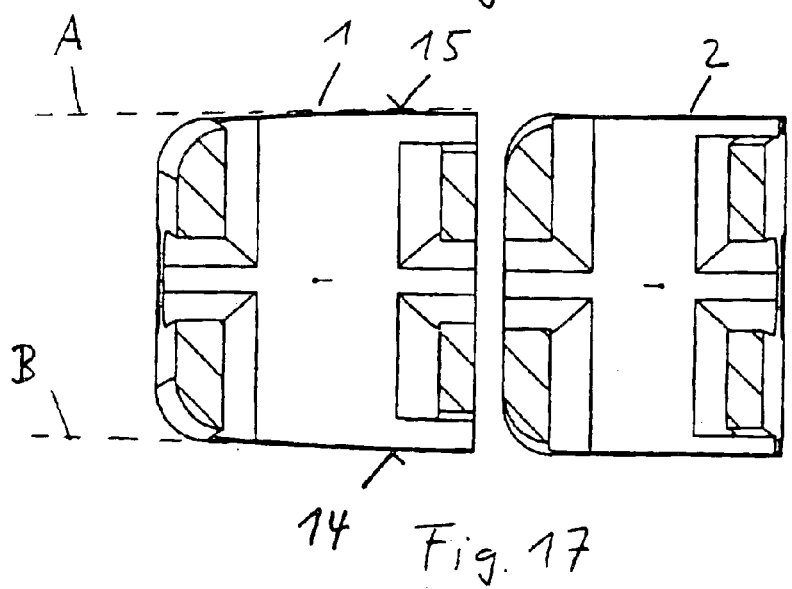

Other advantages of the present invention will be readily appreciated as the same becomes better understood by reference to the following detailed description when considered in connection with the accompanying drawings wherein:

FIG. 1 is a top view of a pair of implants of this invention,

FIG. 2 is a transverse section of vertebrae interspace with both implants in situ, FIG. 3 is a perspective view of the first implant of this invention, FIG. 4 is a plane view of the implant of FIG. 3, from the near lateral side, FIG. 5 is another plane view of the implant of FIG. 3, as will be seen from the coronar view, and showing the preferred orientation of the carbon fibers, FIG. 6 is another plane view of the implant of FIG. 3, FIG. 7 is a perspective view of the second implant of this invention FIG. 8 is a plane view of the second implant of FIG. 7, FIG. 9 is another plane view of the second implant of FIG. 7, FIG. 10 is another plane view of the second implant of FIG. 8, FIG. 11 is a diagrammatic section of a vertebral interspace of a vertebrae column showing the insertion of the first implant, FIG. 12 is a view similar to FIG. 11 illustrating the insertion of the second implant, FIG. 13 is a view similar to FIG. 11 showing the placement of the first implant on the counterlateral side of the disc space, FIG. 14 is a view similar to FIG. 11 showing both implants in situ FIG. 15 a cross-section along line XV—XV of FIG. 1, FIG. 16 a cross-section along line XVI—XVI of FIG. 1, FIG. 17 a cross-section along line XVII–XVI of FIG. 1.

In FIG. 1 the reference number 3 refers to a first implant 1 and a second implant 2. The first implant 1 and the second implant 2 are in the form of a cage as shown in FIGS. 3 and 7. The implants 1 and 2 have a hollow space 28 which is filled with bone graft material, not shown, that will grow out and into the bone tissue of the adjoining vertebrae 4. The implants 1 and 2 are preferably made of radiolucent carbon fiber reinforced polymers or of another rigid biologically acceptable and preferably radiolucent material.

The first implant 1, as shown in FIGS. 1 to 7, has a first saggital wall 5 and a second saggital wall 7. The first saggital wall 5 has a curved outer surface 17 and the second saggital wall 7 a surface 18 that is essentially plane. A posterior wall 9 is provided with a threaded hole 21 extending through the wall 9 for receiving a threaded, positioning tool 38. As illustrated in FIG. 3, the posterior wall 9 has rounded edges 23, 24, 29 and 42. The rounded edge 23 leads to an outer plane surface 18 of the second saggital wall 7 and the rounded edge 24 to an outer curved surface of the first saggital wall 5. The rounded edge 29 leads to a bottom surface 14 and the rounded edge 42 to a top surface 13.

An anterior wall 10 is essentially parallel and in space to the posterior wall 9. The wall has a sharp edge 26 and a rounded edge 27. The sharp edge 26 leads to the plane surface 18 and the rounded edge 27 to the curved outer surface 17, as shown in FIG. 5 to 7.

Two upward strut plates 15 extend between the two saggital walls 5 and 7. These strut plates 15 have sharp edges 15*a* that are in the plane of the surface 18 and that are laterally protruding as shown in FIGS. 3 and 4. Adjoining the first saggital wall 5 outer surfaces 13*a* and 14*a* of the strut plates smoothly adjoin rounded edges 43 that go over the curved outer surface 17.

The second implant 2 is preferably made of the same material as the first implant 1 and is also provided with a hollow space 28 to be filled with bone graft material. A first saggital wall 6 and a second saggital wall 8 are in a spaced relationship with one another and essentially parallel to each other. The first saggital wall 6 has a plane lateral surface 19 and the second saggital wall 8 a curved lateral surface 20. A posterior wall 11 is provided with a threaded opening 21 extending through wall 11 for receiving a threaded, positioning tool 38. As shown in FIGS. 8 and 9, the posterior wall 11 has rounded edges 33, 35, 44, 45 and 21. The rounded edge 33 adjoins the plane surface 19 and the rounded edge 44 adjoins the curved surface 20. The rounded edge 35 adjoins a top surface 46 and the rounded edge 45 a bottom surface 47. As shown in FIGS. 15 to 17, the surfaces 46 and 47 of the implant 2 are parallel to each other. The surfaces 14 and 15 of the cage 1 are inclined as indicated with the dotted lines A and B (FIG. 17). The inclined surfaces 14 an 15 make the insertion of the first implant 1 easier.

An anterior wall 12 is essentially parallel to and in spaced relationship with the posterior wall 11. Wall 12 has rounded edges 34 and 37 that adjoin the plane surface 19, the curved surface 20, the top surface 46 or the bottom surface 47. The posterior wall 11 and the anterior wall 12 have rounded edges similar to edges 34 and 37.

The method of fusing adjoining vertebrae bodies according the present invention is illustrated in FIGS. 11 to 14. The method comprises clearance of the intervertebral disc space and opening the neuroforamen on one side wherein the facet joint is resected and a canal C is opened. Preferably, the disc height can be partially restored by inserting a spreader. In FIG. 11 the left muscle M is not injured.

Into the canal C a first implant 1 is introduced with the help of a positioning tool 38 and then pushed laterally. The first implant 1 has the rounded side R lateral and is designed to go the furthest into the disc space laterally. It tends to restore the disc space like a wedge, which distracts the far lateral annulus and thus further opens the far lateral foramina, decompressing the nerve root.

When the first implant 1 is positioned as shown in FIG. 12, a second implant is introduced in direction of arrow 40 through the same canal C with the help of a positioning tool 38. This second implant 2 has rounded edges $R_2$ on a far lateral side and a flat side $F_2$, that mates with a flat side F of the first implant and pushed the first implant contralaterally into its final position as illustrated in FIG. 13. The lateral force acting on the first implant is indicated with arrow 41. The upward strut plates 16 make the insertion of the second implant 2 into the disc space easier, like rails, but prevent anterior and posterior migration of the implant in its final position.

As already explained, the first and the second implants are asymmetric to each other. Especially the dimensions $D_1$ and $D_2$ as shown in FIG. 1 are different. $D_2$ is preferably smaller. $D_1$ is for example 8 mm and $D_2$ 7 mm. Each implant 1, 2 is designed for what it is to do during its part of insertion. The requirement of each step as shown in FIGS. 11 to 13 is different and therefore so is the implant.

FIG. 14 shows the final position of the implants 1 and 2. The implants 1 and 2 can have the flat sides F and $F_2$ in contact with one another but can also spread from each other.

What is claimed is:

1. A pair of lumbar interbody implants, each of generally rectangular cross-section, adapted to be pushed laterally in the disc space between adjacent vertebrae for spinal, interbody fusion, wherein each implant comprises:
   a first and second saggital wall (5, 7; 6, 8);
   an anterior wall (10) at one end and a posterior wall (9, 11) at the other end;
   said posterior wall (9, 12) has means (21) to receive a positioning tool;
   an upper surface (13) and a bottom surface (14);
   said first and second saggital walls each of which has an outer surface and top and bottom edges, wherein
   a hollow space (28) is located within said walls, said hollow space (28) being adapted to receive therewithin bone graft material; and
   the two implants are asymmetric to each other.

2. A pair of claim 1, wherein a first implant has a first saggital wall with an outer surface that is curved and a second saggital wall that is essentially plane.

3. A pair of claim 2, wherein a second implant has a first saggital wall with an outer surface that is curved and a second saggital wall that is essentially flat.

4. A pair of claim 2, wherein the essentially plane surfaces of the saggital walls are mating surfaces.

5. A pair of claim 1, wherein at least one strut (15, 16) is extending between the two saggital walls.

6. A pair of claim 5, wherein the outer surface of the first saggital wall is spaced from the outer surface of the second saggital wall of the first implant a distance larger than spacing between the two outer surfaces of the second implant.

7. A pair of claim 1, wherein at least one saggital wall of the first cage and one saggital wall of the second cage has a top and a bottom edge each of which is rounded.

8. A pair of claim 1, wherein the implants are in the form of cages.

9. A pair of claim 8, wherein the second cage that is to be inserted second into the disc space has rounded leading edges on a far lateral side.

10. A pair of claim 1, wherein a first implant, that is to be inserted first into the disc space, has a rounded lateral side, which enters first.

11. A pair of claim 1, wherein at least one of the implants has upward struts designed to make insertion of the implants into the disc space easier, and to prevent anterior as well as posterior migration of inserted implant.

12. A pair of claim 1, wherein at least one of the implants is shaped with a posterior portion that is not as high as an anterior portion, providing lordosis.

13. A pair of claim 1, wherein the second implant that is to be inserted second into the disc space, is smaller than the first cage, wherein the height and the length of the two implants are essentially the same.

14. A method of fusing together adjoining vertebrae bodies with a disc space therebetween, which comprises
   clearance of the intervertebral disc space and opening the neuroforamen on one side wherein a spinal canal is opened,
   inserting a first implant, that has a rounded lateral side and a hollow space therein containing bone graft material, the furthest into the disc space laterally,
   introducing a second implant that has rounded leading edges on a far lateral side and a hollow space therein containing bone graft material,
   with this second implant pushing the first implant contralaterally into its first position,
   wherein the second implant is asymmetric to the first implant and either mates with the first implant pushing it further laterally or is closely spaced therefrom.

15. The method of claim 14, wherein the second implant has a flat side mating with one lateral side of the first implant.

16. The method of claim 14, wherein the second implant has a flat side mating with a flat lateral side of the first implant.

17. The method of claim 14, wherein the second implant is smaller than the first implant.

18. The method of claim 14, wherein the first as well as the second implant each has a posterior side that is shorter than an anterior side.

19. The method of claim 14, wherein the two implants are in the form of a cage.

* * * * *